United States Patent
Wieczorek et al.

(10) Patent No.: US 6,187,974 B1
(45) Date of Patent: Feb. 13, 2001

(54) PROCESS FOR PRODUCING UNSATURATED FATTY ALCOHOLS FROM LAURIC OILS

(75) Inventors: Frank Wieczorek, Meerbusch; Gerhard Konetzke, Dessau; Ekkehard Seifert, Rosslau, all of (DE)

(73) Assignee: DHW Deutsche Hydrierwerke GmbH Rodleben, Rodleben (DE)

( * ) Notice: Under 35 U.S.C. 154(b), the term of this patent shall be extended for 0 days.

(21) Appl. No.: 09/262,802

(22) Filed: Mar. 4, 1999

(30) Foreign Application Priority Data

Mar. 11, 1998 (DE) .............................. 198 10 440

(51) Int. Cl.$^7$ .................................. C07C 27/04
(52) U.S. Cl. ........................... 568/885; 568/884
(58) Field of Search .................. 568/884, 885; 554/167, 174, 230

(56) References Cited

U.S. PATENT DOCUMENTS

| | | | | |
|---|---|---|---|---|
| 4,652,406 | * | 3/1987 | Lepper | 260/410.9 |
| 5,514,820 | * | 5/1996 | Assmann | 554/167 |
| 5,672,781 | * | 9/1997 | Koehler | 568/885 |
| 5,917,097 | * | 6/1999 | Koehler | 568/884 |

FOREIGN PATENT DOCUMENTS

| | | |
|---|---|---|
| 43 35 781 A1 | 4/1995 | (DE) . |
| 44 25 180 A1 | 1/1996 | (DE) . |

OTHER PUBLICATIONS

Ralston, "Fatty Acids and Their Derivatives,", pp. 258–321, 492–500, 571–580, 711–728 & 783–793, 1948.*

* cited by examiner

*Primary Examiner*—Michael L. Shippen
(74) *Attorney, Agent, or Firm*—Collard & Roe, P.C.

(57) ABSTRACT

A process is provided for producing unsaturated fatty alcohols from lauric oils, and includes (a) ester interchange of the deacidified lauric oils with methanol to obtain the overall fatty acid methyl ester mixture; (b) fractionation of the fatty acid methyl ester mixture into a $C_{12}$–$C_{16}$-methyl ester (ME) fraction to be used for saturated fatty alcohols, and a $C_{18}$-ME fraction containing the nearly complete proportion of the unsaturated methyl esters (ME); (c) winterization of the $C_{18}$-ME fraction in order to separate out the saturated $C_{18}$-ME component; (d) selective hydrogenation of the unsaturated winterized $C_{18}$-ME fraction to unsaturated fatty alcohols with an iodine number between 90 and 100; and (e) purifying the crude unsaturated fatty alcohols by distillation.

9 Claims, No Drawings

PROCESS FOR PRODUCING UNSATURATED FATTY ALCOHOLS FROM LAURIC OILS

BACKGROUND OF THE INVENTION

1. Field of the Invention

The present invention relates to a process for producing unsaturated fatty alcohols from lauric oils.

2. The Prior Art

As compared to saturated fatty alcohols, unsaturated fatty alcohols are only produced in comparatively small quantities. However, unsaturated fatty alcohols, because of their special properties, are important intermediates for oleochemical derivatives or tensides. They are also directly employed in fields such as the cosmetic and pharmaceutical industries. Derivatives of unsaturated fatty alcohols are also employed in the cosmetic and pharmaceutical fields. They are predominantly employed in the technical sector, for example as auxiliary agents or as components of lubricants, or also in detergents. They are technically produced exclusively from native raw materials by heterogeneously catalytic processes. Here the raw material is specifically selected for defined unsaturated final products, so that important components of the chain length spectrum are already present in the raw material. For example, tallow and lard as well as technical oleins produced from the latter by various concentration methods have been the raw materials for producing unsaturated fatty alcohols. Other raw materials are various vegetable oils with higher iodine numbers such as rapeseed oil, sunflower oil, palm kernel oil, and cottonseed oil.

Vegetable raw materials such as oils with low iodine numbers, the so-called laurics, have been employed for the production of unsaturated fatty alcohols. As compared to animal raw materials, these oils have superior sensorial properties such as odor and color. Their shelf life is much longer due to a lower component of N-containing by-products; and they have fewer color-imparting impurities in the purified raw substances. With lauric oils, the unsaturated components are almost exclusively present in the $C_{18}$-chain length range, which makes their concentration possible.

In industrial practice, a distinction has previously been made between substantially three procedures for producing unsaturated fatty alcohols. In light of the availability of different raw materials or intermediates, these three procedures have each become relatively important:

(1) Direct hydrogenation of triglycerides will produce unsaturated fatty alcohols and a few decomposition products of the glycerin, primarily 1,2-propane-diol. This process has the significant drawback that the glycerin is destroyed and that the decomposition products formed in the process have to be removed by washing or extraction. Furthermore, hydrocarbons are formed in greater amounts and have to be separated in complicated fractionating operations.

(2) Splitting of the oils or fats will produce fatty acids and glycerin. Following separation of the glycerin, esterification of the fatty acids takes place with lower alcohols such as methanol or butanol to obtain the respective esters. Hydrogenation of the esters will produce unsaturated fatty alcohols with the release of the alcohol used for the esterification. This alcohol can be recycled. This procedure is relatively costly in light of the multitude of required stages, as well as due to the requirements in these stages with respect to distillatory purification. The overall process is complicated by the stages both in technical and economical respects.

(3) Ester interchange of the oils and fats with methanol according to various methods can be used to obtain methyl esters, using homogeneous or heterogeneous catalysts. Hydrogenation of these methyl esters can be used to obtain unsaturated fatty alcohols, with recovery and recycling of the methanol.

According to procedure variation (1), unsaturated fatty alcohols are obtained with a composition which is predetermined by the fatty acid spectrum of the oil. Also, the composition can be slightly influenced by selection, partial hydrogenation or crystallization. Where more extensive alterations are possible only in the stage of the alcohols, it is possible in connection with procedure variations (2) and (3) to effect targeted changes in the raw material. These changes can occur both in the preliminary stages of the split fatty acids, distilled fatty acids, or methyl esters, as well as also in the alcohol stage.

The use of lauric oils for producing unsaturated fatty alcohols is known, for example from German Patent Numbers DE 43 35 781 A1 and DE 44 25 180 A1. The lauric oils have a focal point of their C-chain distribution in the $C_{12}$ to $C_{14}$ range. The unsaturated components are almost exclusively present in the $C_{18}$ chain length range, which makes their concentration possible.

DE 43 35 781 A1 describes a process for producing unsaturated fatty alcohols with an iodine number of 20 to 110 from lauric oils. Here the triglycerides contained in the raw materials are split by pressure splitting into the fatty acids, and esterified with methanol, if need be, or converted by ester interchange into fatty acid methyl esters. The fatty acids or fatty acid methyl esters are subsequently hydrogenated to the fatty alcohol. The fatty acid, the fatty acid methyl esters and/or the hydrogenation product are finally fractionated. Prior to fractionation, the iodine number of the product to be fractionated is determined. A defined quantity of the first runnings is withdrawn in the course of fractionation depending on the determined iodine number and the desired one, which raises the iodine number of the fatty alcohol. The drawback of this procedure is mainly that costly fractionating operations are required, and that different coupled fractions are collected, for which only limited possibilities for utilization are available. Furthermore, in the Cle-range it is not possible to separate the $C_{18}:0$ and the $C_{18}:1$ components by distilling, so that only a certain iodine number can be obtained. This process is very costly and consequently uneconomical.

In the process described in DE 44 25 180 A1, the lauric oils are split into fatty acids and glycerin. The separated fatty acids so obtained are subjected to fractionated crystallization. The fraction of unsaturated fatty acids is subsequently esterified to methyl esters, if need be, or finally hydrogenated to unsaturated fatty alcohols with an iodine number of 85 to 100. Such fatty alcohols have very good color and odor properties and are characterized by a particularly advantageous cold behavior. The step of separating saturated and unsaturated fatty acids required in connection with this procedure is preferably feasible by means of a so-called "rewetting" separation. This is known from the separation of tallow fatty acid into stearin and olein. In the separation of the tallow fatty acid by rewetting, the technical fatty acid mixture is cooled to low temperatures, whereby crystallization of the palmitic/stearic acid takes place in the oleic acid with formation of a dispersion. For washing off the oleic acid from the crystals, it is necessary to add to the dispersion an aqueous wetting agent solution, such as a tenside.

By finally centrifuging the emulsion/dispersion in a separator, the latter is separated into an oleic acid phase and a water/saturated fatty acid dispersion. The fatty acid dispersion, the palmitic/stearic acid water dispersion, subsequently has to be heated to about 50° to 80° C. in order to separate the molten palmitic/stearic acid from the aqueous wetting agent solution, which is recycled.

The process stage of separation by rewetting for fractionated crystallization of the split fatty acids obtained according to process step (a) is very time-consuming and requires additional expenditure in terms of equipment. This leads to substantial costs for the final product. Furthermore, when separating split fatty acids by rewetting from lauric oil, it is necessary due to the composition of the lauric oils to separate in a number of process stages a large amount of excess saturated fatty acids with differentiated solidification ranges.

The high content of 80% to 90% saturated $C_{12}$–$C_{18}$-fatty acids can be separated also, instead of by separation through rewetting, by fractionated crystallization with the help of an organic solvent. The solvents such as, for example methanol, methanol/water, acetone or hexane, normally employed in this case as in the case of tallow fatty acid, require for the crystallization process temperatures of $\leq 0°$ C. combined with high dilution. This procedure is very costly and requires high expenditure in terms of equipment for handling and recycling the solvent.

SUMMARY OF THE INVENTION

It is an object of the present invention to provide a process for producing unsaturated fatty alcohols from lauric oils that can be carried out in a very economical way and which permits omitting the process steps of separation by rewetting without adverse effects on the quality of the final products.

The lauric oils form the main raw material based on the native saturated $C_{12}$–$C_{18}$-fatty alcohols used for the detergents industry. These oils permit optimal utilization of the $C_8$-components, which in the case of coconut oil amount to about 11%, and in the case of palm kernel oil come to about 20%. This fraction is particularly suitable for the production of unsaturated fatty alcohols. The different composition of the $C_{18}$-fraction on the basis of palm kernel and coconut oils leads to the fact that both oils are basically suitable. However, the palm kernel oil $C_{18}$-fraction is optimal for the unsaturated fatty alcohols because in this fraction, the ratio $C_{18}:0$, $C_{18}:1$, $C_{18}:2$, $C_{18}:3$ is particularly favorable both for selective hydrogenation and, in the unsaturated fatty alcohol, for the properties of the final product.

The procedure for producing the unsaturated fatty alcohols from lauric oils is described as follows:

(a) Ester Interchange

The ester interchange of the laurics with methanol following deacidifying of the raw material is a process useful for large scale industrial use. In addition to glycerin, this process supplies the chain length distribution of the methyl esters (ME) preformed in the oil.

(b) Fractionation

The first running component of $C_6$- to $C_{10}$-ME is separated first, and subsequently the $C_{12}$–$C_{16}$-ME component for the saturated fatty alcohols. Due to the differences in the boiling point, a $C_{18}$-ME fraction with a total proportion of $C_{18}$-components of >96% is thus collected. It is economically advantageous that the methyl esters with shorter chains do not have to be quantitatively subjected to the costly selective hydrogenation incurring higher costs.

(c) Winterization of the $C_{18}$-ME Fraction

Winterization of the $C_{18}$-ME fraction is carried out without any solvent by lowering the temperature preferably in one but also in several steps to temperatures of $-10°$ C. to $+5°$ C. The formation of a crystal fraction occurs in this range, and the fraction mainly contains the saturated methyl esters in the order of magnitude of 10% to 25%; and their separation is via a suitable filter. Depending on the residual iodine number of the ME crystal fraction, the latter is subsequently converted into derivatives, or preferably transformed into saturated fatty alcohols. Of all tested crystallization processes employed for laurics, the one for $C_{18}$-ME is preferable. This is because after a short dwelling time, a crystal paste with easily filtratable solid particles is formed. This paste can be processed further without any problems. A heatable agitator-equipped crystallization vessel suffices for this reason as equipment for this step. Subsequently, there is a simple filtration process employing, for example a screen or belt filter. If the preferred palm kernel oil is employed, it is possible to produce a $C_{18}$-fraction with a $C_{18}$-ME content of 96.5% to 98.5% by fractionation. It is possible to concentrate the content of saturated methyl esters, mainly the content of $C_{18}:0$-ME from about 10% to 13% to 1% to 4% in the filtrate of the winterization stage.

The crystal paste separated after the winterization stage, which contains the main proportion of $C_{18}:0$-ME, amounts to about 15% to 35% of the amount of the filtrate, and has an iodine number of 30 to 50. No further separation is required because it is preferably employed in the hydrogenation of saturated fatty alcohols. They are mixed with highly unsaturated fatty alcohols to obtain unsaturated fatty alcohols with the 40 to 60 iodine number range. However, if desired, this fraction is accessible to selective hydrogenation and leads to corresponding mixtures of unsaturated and saturated fatty alcohols with low iodine numbers.

If coconut oil is used, a highly unsaturated $C_{18}$-ME fraction is obtained as well, but with a lower yield. Reducing its concentration of $C_{18}$-ME, which is carried out by means of winterization as well, takes a less favorable course and leads to a residual 3% to 6% $C_{18}:0$-ME content in the filtrate.

(d) Selective Hydroaenation

Under conditions which are basically known, the unsaturated ME-fractions are subjected to selective hydrogenation to produce unsaturated fatty alcohols. Thus the maximum content of unsaturated fatty alcohols is obtained in cis-configuration with only small proportions of by-products. Among the various catalyst systems that are suitable for completing the reduction of carboxyl groups while largely preserving the olefinic double bonds in the molecule are heterogeneous zinc oxide/chromium oxide systems partially promoted with activating components such as Zr, Ba, Al. These are preferred in the present case. Such catalyst systems produce unsaturated fatty alcohols with particularly low trans-contents and small proportions of position isomers. The conditions of the continuously carried out hydrogenation process require a pressure of 200 to 300 bar $H_2$ and high temperatures. Here the rate of flow-through of the ester via the catalyst bed at different temperatures is varied in the range of about 0.1 to 0.4 v/vh. It is possible to obtain a reaction of 99.0% to 99.8% ester. For preserving the olefinic double bonds, the ratio of methyl ester to $H_2$ is important in connection with this catalyst system as well, whereby adequate selectivity is obtained when using molar ratios of ME:$H_2$ of $\leq 1:60$.

(e) Purification by Distillation

The small proportions of by-products formed, such as saturated and unsaturated hydrocarbons, as well as the wax esters formed by ester interchange can be separated almost quantitatively as first runnings (1–2%) or residue (1–5%) by simple purification distillation.

By combining the process steps (a) to (e) in the stated sequence, unsaturated fatty alcohol with an iodine number of between 90 and 100 is obtained based on lauric oils by a highly economical procedure. The unsaturated fatty alcohols so obtained represent mixtures of $C_{18}$-alcohols, whereby the proportion of the $C_{18}$:1-fraction, which is the oleyl alcohol, is in excess of 90% by weight. According to the process of the invention, crude fatty alcohols with an iodine number of between 90 and 100 are obtained from palm kernel $C_{18}$-ME or coconut $C_{18}$-ME with the following composition, in which all percents are by weight, in the following

TABLE

|     |          | From palm kernel $C_{18}$-ME | From coconut $C_{18}$-ME |
|-----|----------|------------------------------|---------------------------|
|     | $C_{18}$:0 | 2–3%                         | 3–5%                      |
| cis | $C_{18}$:1 | 87–93%                       | 80–90%                    |
| trans | $C_{18}$:1 | 3–6%                       | 4–8%                      |
|     | $C_{18}$:2 | 2–3%                         | 4–8%                      |
|     | $C_{20}$:0 | 0–2%                         | 0–2%                      |
|     | $C_{20}$:1 |                              |                           |

The solidifying points of the unsaturated fatty alcohols are in the range of 5° C. and 11° C.

The unsaturated fatty alcohols with an iodine number of 90 to 100 so obtained can be mixed with suitable other fatty alcohols to obtain unsaturated fatty alcohols with a defined iodine number range. This range, as a rule, is determined by the field of application of the unsaturated fatty alcohols. Another fatty alcohol suitable for this purpose is, for example a saturated fatty alcohol obtained by hydrogenation From the $C_{12}$–$C_{16}$ methyl ester fraction collected in process step (b). Here the saturated fatty alcohol is split into single cuts by further fractionation and the single cuts are mixed with the unsaturated fatty alcohol.

From the filter cake of the fatty alcohol methyl ester collected in process step (c), it is possible to obtain by selective hydrogenation a partially unsaturated fatty alcohol. This can be used as a mixing component for producing unsaturated fatty alcohols with low iodine numbers.

The economy of the process is additionally enhanced through such useful exploitation of the by-products collected according to the process. In comparison, a treatment of the stearic/palmitic acid collected as by-product according to the known state of the art for the purpose of obtaining a miscible fatty alcohol requires significantly greater financial expenditure.

The unsaturated fatty alcohols produced according to the process of the present invention have the advantageous properties of the products producible from vegetable oils, such as good sensorial properties. For example, in particular, there are excellent color and odor characteristics, good storage stability, and low solidifying points. Therefore, they can be advantageously employed in typical fields of application such as in the cosmetic sector or in the technical field. Thus to some extent they can be used also directly in the form of derivatives, for example as oxethylates, sulfates and ether sulfates, such as for detergents, technical cleaning agents or auxiliary agents.

DETAILED DESCRIPTION OF PREFERRED EMBODIMENTS

Other objects and features of the present invention will become apparent from the following detailed description considered in connection with the accompanying examples which discloses several embodiments of the present invention. It should be understood, however, that the examples are designed for the purpose of illustration only and not as a definition of the limits of the invention.

EXAMPLE 1

(a) Ester Interchange From Palm Kernel Oil (PKO)

A 4-liter glass flask equipped with "KPG" agitator, thermometer, drip-feed funnel, cooler, vacuum adapter and distillate receiver was loaded with 2500 g of a commercially available whole PKO-raffinate. This was dried for 30 minutes at 90° C. and about 35 mbar, cooled to 60° C., and 695 g methanol was then added first, and subsequently 55 g Na-methylate solution 30% was added. The content of the flask was stirred for 1 hour at 50° C. and subsequently transferred into a separation funnel. After about 45 minutes, 2662 g top phase (crude ester) and 560 g bottom phase (glycerol, methanol) had separated.

The top phase was washed three times with 320 ml drinking water at about 50° C., and subsequently dried for 30 minutes at 80° C. and about 35 mbar. 2395 g palm kernel oil methyl ester (PKO-ME) (crude) was obtained and had an acid number (AN) of=0.06. The C-chain spectrum corresponded largely with the PKO.

(b) Fractionation of the PKO-ME 2300 g dried PKO-ME was fractionated via a column filled with wire coils at a reflux ratio of 3:1. The following $C_{18}$-ME fraction was separated at 0.5 mbar in the 1550 to 170° C. boiling range:

Saponification number (SN)=184.7 Iodine number (IN)= 83.3 C-chain distribution:

$C_{16}$=0.4%; $C_{18}$:0=11.5%; $C_{18}$:1=80.7%; $C_{18}$:2=6.4%; $C_{20}$=0.8%.

(c) Fractionated Crystallization (winterization)

For winterization, a jacket-cooled cylindrical glass vessel with a volume of about 200 cc and a slowly operating agitator traveling along the wall was used. The solids proportion was filtered off in a jacket-cooled vacuum filter with a medium-hard filter. The filter surface area=abt. 35 cm$^2$; and the filter temperature corresponded with the winterization temperature. After filling the vessel with 150 g $C_{18}$-ME at about 30° C., cooling was carried out under stirring at a rate of about 1° C. per minute. Crystallization was carried out for 15 to 45 minutes after the winterization temperature had been reached.

By fractionated crystallization at +5° C. and a stirring time of 15 minutes, 13% filter cake with an IN of=27.1 and the following C-chain distribution was separated from the $C_{18}$-ME fraction:

$C_{16}$=0.5%; $C_{18}$:0=69.4%; $C_{18}$:1=27.4%; $C_{18}$:2=1.6%; $C_{20}$=1.1%.

The filtrate proportion amounted to 87.7% with the following characteristics: IN=88.5%; C-chain distribution: $C_{16}$= 0.3%; $C_{18}$:0=3.2%; $C_{18}$:1=88.5%; $C_{18}$:2=7.2%; $C_{20}$=0:8%.

(d) Selective Hydrogenation

The winterized $C_{18}$-ME was selectively hydrogenated in a continuously operated high-pressure reactor on an activated ZnO $Cr_2O_3$ catalyst. The hydrogenation conditions were as follows: 285° C., 240 bar $H_2$-pressure; 0.1 v/vh $C_{18}$-ME, and a molar ratio of $C_{18}$-ME to $H_2$ of 1:100.

(e) Purifying Distillation

The discharge obtained from the hydrogenation reactor, which was freed from the methanol, was subjected to a purifying distillation at a pressure of 0.5 bar, whereby 1.2% first runnings (FR) was separated; 3.5% remained in the distillation residue. The resulting $C_{18}$-UFA-MR (UFA= unsaturated fatty alcohol; MR=main runnings) only had an extremely weak odor and it was colorless (APHA=10). The carbonyl content came to 53 mg/kg and, after 1 month of storage without $N_2$-cover increased only by about 10 units. The characteristics and the C-chain spectrum of the $C_{18}$-UFA-MR were as follows:

AN=0.08; SN=0.5; IN=94.1, OHN (hydroxyl number)=209.3; $H_2O$ (K.F.)=0.03% (K.F.=analytical method according to Karl Fischer); SP (=solidifying point)=10.1° C.; HC-content (=hydrocarbon) <0.1%.

$C_{16}$=0.2%; $C_{18}$:0=4.3%; $cisC_{18}$:1,=86.5%; $transC_{18}$:1=3.8%; $C_{18}$:2=4.3%; $C_{18}$total=98.9%; $C_{20}$=0.9%.

The UFA-MR with an iodine number 94.1 so obtained was mixed with saturated fatty alcohol (SFA) with the C-chains $C_{12}$, $C_{14}$, and $C_{16}$ each with a purity of at least 98%, so-called single cuts, to obtain an unsaturated fatty alcohol (UFA) with a low iodine number. The following UFA's were obtained:

UFA 1: IN=72.5; OHN (hydroxyl number)=214.9; SP=19.8° C. from 0.3% $C_{12}$+2.7% $C_{14}$+20.0% $C_{16}$+77.0% $C_{18}$-UFA-MR.

UFA 2: IN=84.0; OHN=213.0; SP 11.1° C., from 1.0% $C_{12}$+4.0% $C_{14}$+5.7% $C_{16}$+89.3% $C_{18}$-UFA-MR.

The unsaturated fatty alcohols (UFA's) so obtained have excellent sensorial properties, i.e., they are almost odorless and clear like water.

EXAMPLE 2

The procedure was carried out analogous to Example 1, whereby only the process parameters of process stage (c) (=winterization stage) were changed as follows: Winterization of the $C_{18}$-ME fraction was carried out at a temperature of −2° C. and with a stirring time of 20 minutes. 21.3% filter cake was separated, which had an IN of=47.8 and the following C-chain distribution:

$C_{16}$=0.1%; $C_{18}$:0=47.5%; $C_{18}$:1=48.1%; $C_{18}$:2=3.7%; $C_{20}$=0.6%.

The filtrate with a yield of 78.7% was characterized as follows: SN (saponification number)=188; IN (iodine number)=92.6. C-chain distribution: $C_{16}$=0.5%; $C_{18}$:0=1.8%; $C_{18}$:1=89.5%; $C_{18}$:2=7.2%; $C_{20}$=0.9%.

1.5% first runnings was withdrawn after the purifying distillation; 3.9% remained as distillation residue. The $C_{18}$-UFA main runnings obtained was characterized as follows: AN=0.06; SN 0.4; IN=95.7; OHN=209.5; $H_2O$ (K.F.)=0.01%; Sp=5.2° C., HC content=<0.1%; APHA-color=8.

$C_{16}$=0.3%; $C_{18}$:0=2.6%; $cisC_{18}$:1=87.9%; $transC_{18}$:1=3.7%; $C_{18}$:2=4.4%; $C_{18}$total=98.6% $C_{20}$=1.1%.

The $C_{18}$-UFA-MR (MR=main runnings) had an iodine number (IN) of 95.7 and a $C_{18}$:0-content of only 2.6%, which jointly determines the comparatively low Sp (solidifying pt) of 5.2° C.

This means that the $CL_8$-UFA is particularly well-suitable for producing an unsaturated fatty alcohol (UFA) in the 90 to 95 or 80 to 85 IN-range by mixing it, for example with single cuts of a saturated fatty alcohol (SFA). The following unsaturated fatty alcohols (UFA's) were obtained by mixing:

UFA 3: IN=91.9; OHN=210.5; Sp=6.6° C.; obtained by mixing 4.0% $_{16}$+96 0% $C_{18}$-UFA-MR (MR=main runnings)

UFA 4: IN=84.0; OHN=213.5; Sp=9.2° C.; obtained by mixing 1.0% $C_{12}$+4.0% $C_{14}$+7.2% $C_{16}$+87.8% $C_{18}$-UFA-MR (main runnings).

UFA's 3 and 4 have good sensorial properties, which are analogous to those of UFA's 1 and 2 produced according to Example 1.

The filter cake (FC) separated in process stage (c) (=winterization stage) has a $C_{18}$:0 proportion of 47.5% and an iodine number (IN) of 47.8. The filter cake ME was selectively hydrogenated on contact with a $ZnO/Cr_2O_3$-catalyst, whereby the olefinic double bond was largely preserved, and subsequently subjected to a purifying distillation analogous to process step (e) in Example 1, whereby 1.3% first runnings (=FR) was separated; the remaining distilling residue came to 2.8%. The resulting UFA main runnings of the filter cake had the following quality:

AN=0.04; SN=0.2; IN=51.0; OHN=208.7; Sp=38.8° C.; HC (hydrocarbons)=0.1%.

C-chain distribution: $C_{16}$=0.4%;. $C_{18}$=48.1%; $C_{18}$:1=48.9%; $C_{18}$:2=2.0%; $C_{20}$=0.6%.

As compared to an unsaturated fatty alcohol (UFA) of the usual market quality with an IN of about 50, this UFA has a higher solidifying point (Sp), but it is nonetheless well-suitable for mixing with other fatty alcohols for producing unsaturated fatty alcohol (UFA) in the IN-range of <60. By mixing an amount of 37% of said UFA main runnings filter cake (MR-FC), 35% of the $C_{18}$-UFA-MR with an IN=95.7, prepared according to Example 2, as well as 0.5% $C_{12}$, 2.5% $C_{14}$, and 25% $C_{16}$ saturated pure fatty alcohols as so-called single cuts, the following UFA 5 was prepared, with an iodine number of 52.4:

UFA 5 : IN=52.4; OHN=216; APHA=10; Sp=33.1° C.
C-chain distribution: $C_{12}$=0.5% $C_{14}$=2.6%; $C_{16}$=25.2%; $C_{18}$=71.1%; $C_{20}$=0.6%.

EXAMPLE 3

(a) Ester Interchange of Coconut Oil (CNO)

A commercially available whole coconut raffinate was used. The ester interchange was carried out under conditions analogous to those utilized in Example 1. 2380 g CNO-ME (crude) with SN=256.8 and IN=8.0 was obtained from 2500 g CNO. The C-chain spectrum was almost identical with the employed CNO.

(b) Fractionation: of the CNO-ME (crude)

2300 g CNO-ME (dried) was fractionated via a column filled with wire coils at a reflux ratio of 4:1. Due to the lower $C_{18}$-component in the CNO-ME (as compared to the PKO basis), 11.7% $C_{18}$-ME fraction was obtained at 0.8 mbar in the 152° to 172° C. boiling range with the following quality:

AN=0.08; SN=188.6; IN=76.9.

$C_{16}$=1.2%; $C_{18}$:0=19.5%; $C_{18}$:1=66.910; $C_{18}$:2=11.8%; $C_{20}$=0.6%.

(c) Fractionated Crystallization of the $C_{18}$-ME (=winterization)

Winterization was carried out analogous to the procedure utilized in Example 1. By fractionated crystallization at +5° C. and with a stirring time of 30 minutes, 24.1% filter cake (FC) with an IN of=33.2 and the following carbon chain distribution was obtained from the $C_{18}$-ME fraction:

$C_{16}$=2.1%; $C_{18}$:0=67.6%; $C_{18}$:1=21.6%; $C_{18}$:2=8.3%; $C_{20}$=0.4%; as well as 75.9% filtrate with an IN of=92.5 and the following carbon chain distribution:

$C_{16}$=1.0%; $C_{18}$:0=4.2%; $C_{18}$:1=81.3%; $C_{18}$:2=12.9%; $C_{18}$total=98.8%; $C_{20}$=0.6%.

(d) Selective Hydrogenation

The conditions for the selective hydrogenation of the $C_{18}$-ME filtrate corresponded with those utilized in Example 1.

(e) Purifying Distillation

In the purifying distillation of the methanol-free crude alcohol, 1.6% first runnings (FR) was withdrawn at 0.6 mbar; 3.1% remained in the distillation residue.

The $C_{18}$-UFA main runnings (MR) so obtained had the following quality:

AN=0.05; SN=0.5; IN=95.1; OHN=209.5; APHA=15; Sp=10.2° C. CO-content=82 ppm; $H_2O$ (K.F.)=0.03%; hydrocarbon (HC) content=0.11%.

$C_{18}$=0.4%; $C_{18}$:0=3.9%; cis$C_{18}$:1=84.7%; trans$C_{18}$:1=3.2%; $C_{18}$:2=6.7%; $C_{18}$total=98.5%; $C_{20}$=1.1%.

The resulting $C_{18}$-UFA-MR (main runnings) was mixed with so-called single cuts of saturated pure fatty alcohols to obtain an unsaturated fatty alcohol of the usual market quality. The following was used for mixing: 0.4% $C_{12}$+2.8% $C_{14}$+20.3% $C_{16}$+76.5% $C_{18}$-UFA-MR (main runnings). Obtained was an UFA in the 70 to 75 IN-range with the following quality:
IN=72.8; OHN=215.1; Sp=18.9° C.
$C_{12}$=0.4%; $C_{14}$=2.8%; $C_{16}$=20.5%; $C_{18}$=75.5%; $C_{20}$=0.8%.

Accordingly, while a few embodiments of the present invention have been shown and described, it is to be understood that many changes and modifications may be made thereunto without departing from the spirit and scope of the invention as defined in the appended claims.

What is claimed is:

1. A process for producing unsaturated fatty alcohols from a starting raw material containing lauric oils, comprising the steps of:
   (a) converting deacidified lauric oils by ester interchange with methanol into a total fatty acid methyl ester (ME) mixture;
   (b) separating the fatty acid methyl ester mixture by fractionation into a $C_{12}$–$C_{16}$-methyl ester (ME) fraction containing saturated fatty alcohols, and into a $C_{18}$-ME-fraction containing nearly the complete proportion of the unsaturated methyl esters (ME);
   (c) subjecting the $C_{18}$-ME fraction to a solvent-free fractionated crystallization, winterization, for separating out the saturated $C_{18}$-ME fraction from the remaining winterized unsaturated $C_{18}$-ME fraction;
   (d) subjecting said winterized unsaturated $C_{18}$-ME fraction to selective hydrogenation to produce unsaturated fatty alcohols with an iodine number between 90 and 100; and
   (e) purifying crude unsaturated fatty alcohols obtained according to process step (d) by distillation.

2. The process according to claim 1, comprising
mixing purified unsaturated fatty alcohol with suitable other fatty alcohols to obtain unsaturated fatty alcohols with an iodine number in a range of 50 to 95.

3. The process according to claim 2, comprising
hydrogenating the $C_{12}$–$C_{16}$ methyl ester fraction obtained according to process step (b) to produce saturated fatty alcohols; and
splitting by fractionation the saturated fatty alcohols into single cuts, and using said single cuts as said other fatty alcohols for mixing with the unsaturated fatty alcohols.

4. The process according to claim 2, comprising
selectively hydrogenating a filter cake of the fatty acid methyl ester collected according to process step (c); and
using the partially saturated fatty alcohols as said other fatty alcohols for mixing with the unsaturated fatty alcohols.

5. The process according to claim 1, comprising
carrying out the fractionated crystallization under conditions leading to a filtrate component of 70% to 80% by weight based upon the total weight and a $C_{18}$:0 content of 1.5% to 3.5% by weight based upon the filtrate weight.

6. The process according to claim 1, comprising
carrying out the fractionated crystallization at a temperature of +5° C. to −10° C.

7. The process according to claim 1, comprising
employing a fixed-bed catalyst consisting of an activated, thermally pretreated $ZnO/Cr_2O_3$-system for the selective hydrogenation.

8. The process according to claim 1, comprising
using refined palm kerne-l oil as the starting raw material.

9. The process according to claim 1, comprising
using refined coconut oil as the starting raw material.

* * * * *